United States Patent [19]

Geiller

[11] Patent Number: 5,663,511
[45] Date of Patent: Sep. 2, 1997

[54] METHOD AND DEVICE FOR TAKING SAMPLES OF LIQUIDS WITH DIFFERENT VISCOSITIES FROM A DRUM OR OTHER CONTAINER

[75] Inventor: Jean-Paul Geiller, Guerting, France

[73] Assignee: Houilleres Du Bassin De Lorraine, France

[21] Appl. No.: 512,573

[22] Filed: Aug. 8, 1995

[30] Foreign Application Priority Data

Aug. 10, 1994 [FR] France ................. 94 09898

[51] Int. Cl.$^6$ ................................................. G01N 1/14
[52] U.S. Cl. ................................................. 73/864.62
[58] Field of Search .......... 73/863.81, 863.83–863.85, 73/864.51, 864.62, 864.63, 864.22, 864.24, 864.73

[56] References Cited

U.S. PATENT DOCUMENTS

| | | |
|---|---|---|
| 1,950,854 | 3/1934 | Lerch. |
| 2,255,369 | 9/1941 | Spaeth. |
| 3,115,782 | 12/1963 | Echtler, Jr.. |
| 3,277,723 | 10/1966 | Bodman et al. ............ 73/864.62 |
| 4,318,885 | 3/1982 | Suzuki et al. ............ 73/864.22 |
| 4,612,815 | 9/1986 | Green et al. ............ 73/864.51 |
| 5,139,654 | 8/1992 | Carpenter ............ 73/864.62 |

FOREIGN PATENT DOCUMENTS

| | | | |
|---|---|---|---|
| 718955 | 2/1932 | France. | |
| 2423767 | 11/1979 | France. | |
| 0824569 | 12/1951 | Germany | ............ 73/863.83 |
| 4211633 | 10/1993 | Germany. | |
| 9417386 | 8/1994 | WIPO. | |

Primary Examiner—Robert Raevis
Attorney, Agent, or Firm—VanOphem, Meehan & VanOphem, P.C.

[57] ABSTRACT

A device for taking a sample of fluid from a drum includes a dip-tube having at its lower end a closure member, a piston having at the end of a rod a disk adapted to slide in the dip-tube, to which it is sealed, and members for temporarily positioning the piston disk in the heightwise direction. A support ring is adapted to rest on the periphery of the filler orifice of a substantially horizontal wall of the drum and has a passage in which the dip-tube slides and to which the dip-tube is sealed, the disk remains inside the dip-tube at all times, and the closure member is in the form of a fixed end-piece in which is provided an orifice provided with non-return means enabling fluid to be aspirated into the tube but preventing the fluid from escaping under it own weight.

20 Claims, 3 Drawing Sheets

METHOD AND DEVICE FOR TAKING SAMPLES OF LIQUIDS WITH DIFFERENT VISCOSITIES FROM A DRUM OR OTHER CONTAINER

BACKGROUND OF THE INVENTION

1. Field of the Invention

The present invention relates to a method and device for taking samples of liquids with different viscosities from a drum or other container.

2. Description of the Prior Art

Industry at large produces all kinds of liquid waste, in particular oils, hydrocarbons and chemical products. At present it is very difficult if not impossible to precisely define the proportions of the various constituents of the contents of a drum, especially if products with different densities and viscosities are mixed together.

At present, methods for identifying the content of a drum are somewhat erratic. They entail:

- either inserting a dip-stick (a rigid rod or a metal wire) into the drum to extract thereon a product to be identified; this method is somewhat rudimentary and inaccurate;
- or, in a more effective method, taking samples by dipping a tube into the drum. When enough of the tube is immersed, the end remaining in the open is blocked off, the tube is rapidly extracted and the sample is collected in a flask. This method is irksome if samples are to be taken properly since it is essential to clean or to replace the tube before taking the next sample.

However simple they might appear, these methods give only a vague idea of the content of the drum, especially if it contains mixed products with different viscosities. Syringes offer the advantage of much cleaner working conditions, but there remains the problem of sampling the constituents of the content of the drum in equal proportions. What is more, the use of syringes necessarily entails the use of a flexible hose which is soiled in each operation and therefore cannot be used for taking the next sample.

German Patent No. 4,211,633 discloses a sampling device including a piston in the form of a disk and a rod and a dip-tube inside which the cylinder can slide and to which it is sealed. A vertical rod is mounted at the side of the dip-tube and its lower end is fixed to a peripheral portion of a closure disk which, depending on the annular position of the rod about its longitudinal axis, exposes or closes off the lower end of the dip-tube. The enclosure has no top wall. In use, the piston rod (and thus the piston disk) is positioned relative to the enclosure (merely by suspending it, it would seem); by rotating the rod, the closure disk is offset to the side and the dip-tube is lowered to the bottom of the drum; the closure disk is then returned to the closure configuration. One drawback of this solution is that it allows only somewhat unreliable and somewhat impractical sampling of the content of the drum in the heightwise direction: when the dip-tube is lowered with the closure disk in the offset configuration there is a tendency for the tube to tilt away from a vertical configuration and the materials are strongly displaced from under the disk so that the liquid is stirred with the result that the liquid is seriously disturbed just when a reliable sample is required. The sampling device also necessarily pollutes all its exterior surfaces, which may require time-consuming and careful washing before each use. Less importantly, there is nothing to enable the taking of samples at different levels.

U.S. Pat. No. 3,115,782 concerns taking samples from a flow of liquid. It proposes a device including, disposed transversely to a flow pipe, a tube and a piston rod carrying at least two piston disks, one of which is an end disk. The tube is mounted in a retaining ring removably fixed to a transverse section of the pipe; the tube slides in and is sealed to the ring and the disks are adapted to slide in the tube, to which they are sealed. To take a sample the rod is moved across all of the section of the pipe until the end disk abuts against the inside wall opposite the transverse pipe. The flow is allowed to stabilize and then the tube is slid in the same way to trap a sample inside the tube (or a plurality of samples if there are more than two disks). The presence of the rod and the disk necessarily causes significant disturbance of the sample; further disturbances are caused by the lowering of the tube. It is important to note that this sampling device is intended for sampling a flowing liquid and that its use in a static mass would cause unacceptable disturbances during lowering of the rod and the disks to the bottom, as this would cause stirring throughout the volume through which the disks pass: taking a sample in this stirred volume would then yield results that would not be representative of the situation prior to stirring. Less importantly, this sampling device offers no adjustment of the height at which the sample is taken. As the sample is taken from on top of the terminal disk and around the rod, these parts are soiled as each sample is taken.

Note that all these prior art methods concern themselves very little with the risk of accidents or pollution connected with the manipulation of hazardous chemical products.

The invention proposes to remedy all these drawbacks by a method which aspirates and forces fluid into a vacuum chamber so that the fluid content (for example the static fluid content) of a drum or other container can be sampled simply and quickly, advantageously at a level that can vary, whether the fluid to be sampled is of liquid or paste-like consistency, without altering the proportions of the various constituents and with provision for scraping and cleaning parts in contact with the fluid so that successive samples of varied products can be taken without significant pollution of the drums or sample flasks by each other.

SUMMARY OF THE INVENTION

To this end the invention proposes a device for taking samples of fluid from a drum filled with a mass of fluid up to a given level and having a substantially horizontal wall provided with a filler orifice, including:

- a dip-tube, or columnar member, having a closure member at its lower end;
- a piston including at the end of a piston rod a disk or segment adapted to slide in the dip-tube, to which it is sealed; and
- means for temporarily positioning the piston disk in the heightwise direction so that this disk remains at a given distance from the surface of the fluid mass.

The device includes a support ring adapted to rest on the periphery of the filler orifice and has a passage having on the inside thereof at least one scraper seal in which the dip-tube is adapted to slide, and to which it is sealed. Relative movement between the piston and the dip-tube is such that the disk remains at all time in the dip-tube. Further, the closure member is formed as an end-piece fixed to the lower end of the dip-tube, in which an orifice is provided with non-return means enabling fluid to be aspirated into the tube but preventing fluid from escaping therefrom under its own weight.

The simple and reliable nature of a structure of this kind will be evident, as will the minimal disturbance during the taking of samples and the minimal risk of soiling, in particular by virtue of the fact that, in combination, only the lower face of the disk comes into contact with the fluid, the presence of the non-return means enables the fluid to be aspirated through the end-piece while preventing the fluid from dropping out (which does not exclude forced discharge by means of the piston in some embodiments), and in practice the ring scrapes the outside wall of the tube clean when the tube is removed. Simplicity of use results from the fact that it is easy to lower the components of the sampling device into the fluid (there is no lateral offset) and from the fact that no particular maneuver is required to prevent the fluid from escaping. A simple to-and-fro movement is therefore sufficient. The suction effect as the tube is lowered, without lateral projections, makes sampling reliable.

In accordance with preferred features of the invention, some of which may be combinable with others:

- the piston rod is part of a generally inverted U-shaped member of which one branch is constituted by the rod and another branch has at its lower end a bearing surface adapted to bear on a reference surface for the support ring, the branches being linked by the positioning means;
- the bearing surface is adapted to bear on the wall of the drum;
- the other branch is adapted to slide in a guide sleeve attached to the support ring at a distance from the passage;
- the sleeve includes a longitudinal slot and the other branch includes holding means projecting radially from the sleeve through the slot;
- the reference surface is linked to the support ring;
- the two branches of the U-shaped member are fastened together;
- the two branches of the U-shaped member are provided with means for adjusting their relative position;
- the other branch includes at its upper end a sleeve adapted to receive the piston rod which slides in it and is provided with clamping means;
- the support ring has on its lower face at least two annular centering steps matching at least two filler orifice diameters;
- the support ring includes an externally screwthreaded skirt;
- the dip-tube and the piston rod are provided with temporary fixing means;
- the aspiration end-piece includes a hole constituting an aspiration hole and a discharge hole;
- the hole has a diameter chosen according to the viscosity of the fluid mass to enable aspiration and discharge of the sample by relative disk/tube movement while preventing the sample from escaping under its own weight;
- the hole is formed in a split elastic seal and is flanked by one or more lips;
- the hole is closed by an anti-leak valve incorporating an opening member accessible from the outside;
- the discharge hole is in the wall of the tube near its upper end so that it is separated from the aspiration end-piece by the disk over only part of the relative sliding travel between the disk and the tube, a second piston disk provided with a non-return valve being provided in the tube under the disk to force discharge of the fluid sample by upward movement; and the second disk constitutes the aspiration end-piece.

The invention also proposes a method of taking a sample of fluid from a drum filled with a mass of fluid up to a given level whereby a dip-tube is immersed in the fluid mass which has at its lower end an entry orifice. By sliding the tube around a disk to which it is sealed with the distance between the disk and the surface of the fluid mass kept constant, the dip-tube is removed from the fluid mass with the disk held in a fixed position relative to the tube, and the content of the tube between the end-piece and the disk is expelled through a discharge hole.

The disk remains inside the tube at all times, the fluid is caused to enter the tube during the immersion movement by forced aspiration through a closure member including an orifice provided with non-return means preventing escape of the fluid under its own weight, and the dip-tube slides inside a scraper ring fixed at least temporarily to the disk.

The disk is preferably positioned substantially level with the surface of the fluid mass.

Objects, features and advantages of the invention will emerge from the following description given by way of non-limiting example with reference to the appended drawings.

DETAILED DESCRIPTION OF THE PREFERRED EMBODIMENT

Figure 1:
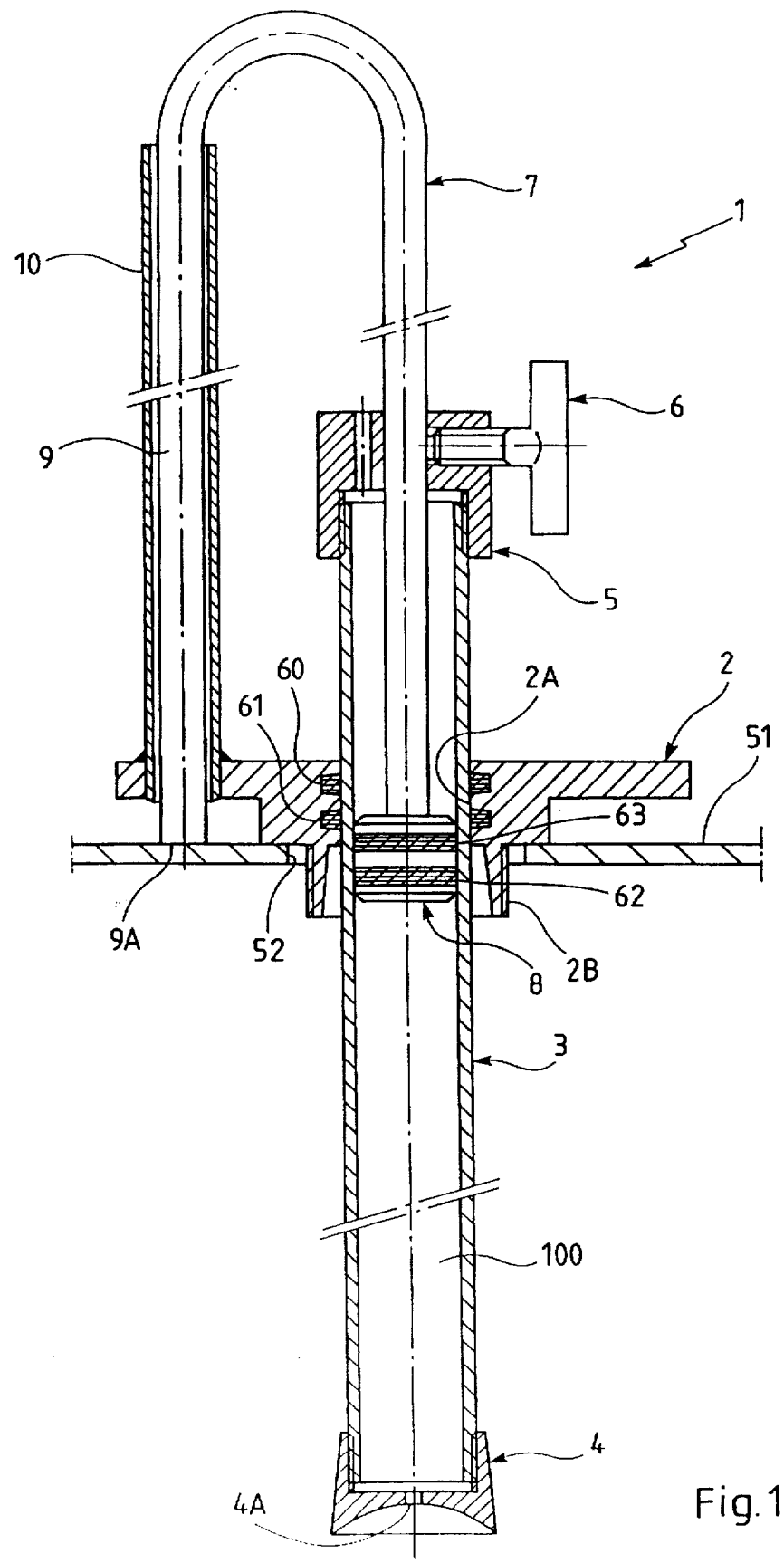
FIG. 1 is a view in vertical section of a sampling device of the invention.

A sampling device 1 shown in FIGS. 1 and 2A through 2C includes:

- a support cup or ring 2 adapted to rest on the periphery of a filler orifice 52 in a drum or container 50 having a substantially horizontal wall 51; a passage 2A in this cup has at least one seal 60 on the inside (in this example there is also a second seal 61);
- a body or dip-tube 3 adapted to slide in the passage 2A, to which it is sealed, and carrying an aspiration end-piece 4 at its lower end; accordingly, the ring 2 scrapes/ cleans the exterior surface of the dip-tube 3; as described below, the dip-tube further includes a discharge hole, in this example constituted by an aspiration hole 4A in the end-piece: the dip-tube 3 is closed at the top by a cap 5 with a hole in it and incorporating a clamping screw 6;
- a piston including, at the end of a piston rod 7, a disk 8 adapted to slide inside the dip-tube 3, to which it is sealed, and to this end provided with seals, in this example two seals 62 and 63; and members for positioning the disk 8 relative to the support ring so that the disk is at a given distance from the surface of a mass of fluid 53 contained in the drum 50.

The passage 2A, the dip-tube 3 and the disk 8 are circular in this example. It is naturally possible to choose an alternative shape, for example a polygonal shape (square, rectangular, octagonal or otherwise), for reasons of guidance, for example.

The piston rod 7 is preferably part of a member, the general shape of which is that of an inverted U, one branch consisting of the piston rod 7 and the other branch 9 having at its lower end a bearing surface 9A (in this example this is its edge) adapted to bear on a reference surface at least temporarily fixed to the support ring 2.

In the example of FIGS. 1 and 2A through 2C the branches 7 and 9 are parts of a single member with the result that the position of the disk 8 relative to the bearing surface 9A is fixed once and for all; these branches are preferably the same length so that the disk 8 is substantially level with the bearing surface or edge 9A; in other words, the disk is substantially level with the reference surface.

In this example the reference surface is the wall 51, in the immediate vicinity of the filler orifice 52.

Figure 2A:
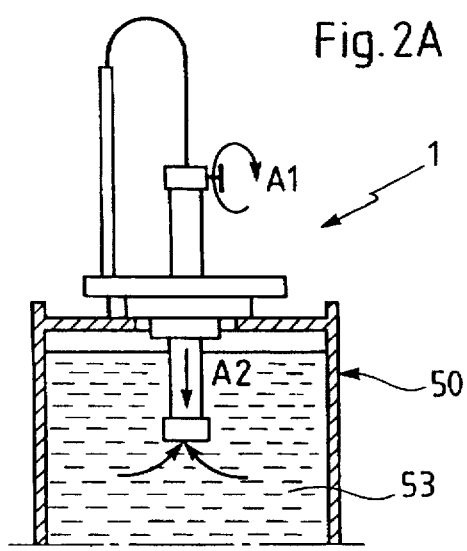
FIGS. 2A, 2B and 2C are diagrammatic views which in conjunction illustrate the operation of the device from FIG. 1.
Figure 2B:
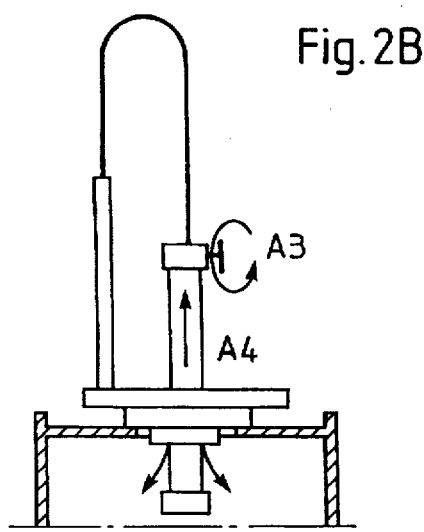
Figure 2C:
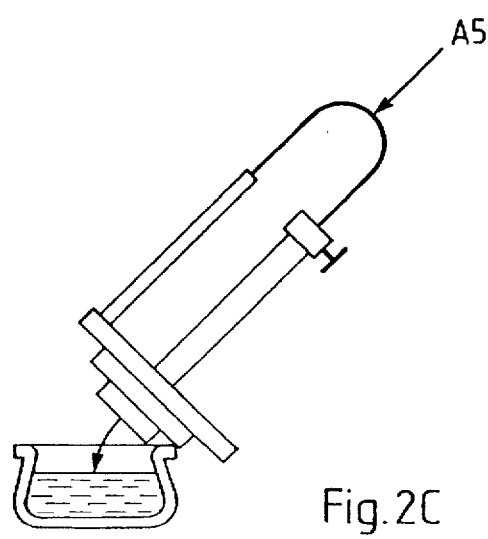

In the example of FIGS. 1 through 2C, the ring 2 advantageously includes a lateral lug to which is fixed a sleeve 10 to guide sliding of the branch 9, at a lateral distance from the passage 2A.

In an alternative embodiment that is not shown the reference surface could be attached directly to the ring 2 itself.

In use, as shown in FIGS. 2A through 2C, to take a sample (for example 200 liters) from the drum 50 the device 1 is placed on the drum 50 with the support cup 2 over the filler orifice 52. The bearing surface 9A of the branch 9 rests on the horizontal wall or top 51 of the drum, so immobilizing the disk 8. After unscrewing the clamping screw 6 in the cap 5 (action A1), the body 3 is pushed down into the drum (action A2). A filler chamber 100 delimited by the piston 8, the body 3 and the end-piece 4 fixed to the end of the body 3 dipping into the container, the volume of which is initially substantially zero, is filled progressively with fluid aspirated through the hole 4A. The section of the aspiration hole 4A is in theory less than that of the interior of the body 3. Because the filler chamber 100 of the body 3 is sealed by the seals 62 and 63 (in this example these are square in section) of the disk 8, suction is generated inside the filler chamber 100 which aspirates the various constituents in the drum through the aspiration hole 4A as the body 3 is inserted to the required depth, for example to the bottom of the drum, producing an accurate average sample (see FIG. 2A).

At this stage of the operation a perfect core sample of the drum contents is contained in the filler chamber 100 of the body 3 between the disk 8 and the end-piece 4.

To immobilize the disk 8 in the dip-tube 3 the screw 6 on the cap 5 is tightened (action A3) after which the body 3 is extracted from the drum by sliding it through the cup 2 which is held onto the drum (action A4). Immobilizing the piston rod 7 relative to the cap 5 by means of the screw 6 enables the body 3 to be raised with the disk 8, the effect of which is to retain the sample inside the filler chamber 100, the aspiration hole 4A in the end-piece 4 being sized so as not to allow the product to escape (the size of the hole allows for the viscosity of the product).

Note that as the body 3 is extracted through the cup 2, its outside is cleaned over all of its length by virtue of the seals 60 and 61 disposed in the cup 2 where the body 3 passes through it (FIG. 2B), which are preferably square in section.

At this stage the hole 4A is moved over the sample flask, the screw 6 is loosened and the disk 8 is lowered to drain the chamber 100 of the body 3 totally (action A5 in FIG. 2C).

When the disk has completed its full travel, the device is clean both on the inside and on the outside, and therefore ready to take another sample.

The filler chamber 100 has a capacity of 500 ml for taking samples from drums 870 mm high, for example.

The capacity of the sampling chamber can vary according to the products to be sampled and the volume of the container. All that is required is to modify accordingly the dimensions of the various components of the device described above by way of non-limiting example.

The above description assumes that the drum 50 is full so that the disk 8 is more or less level with its surface.

When taking samples from drums that are not completely full, the air contained in the chamber 100 of the body 3 can impede the absorption of thick products. It is then beneficial to modify the piston rod 7 so that the disk 8 can be positioned level with the product absorbed.

To do this the U-shaped member in FIG. 1 can be modified so that the branch constituted by the piston rod 7 is longer than the branch 9.

Figure 3A:
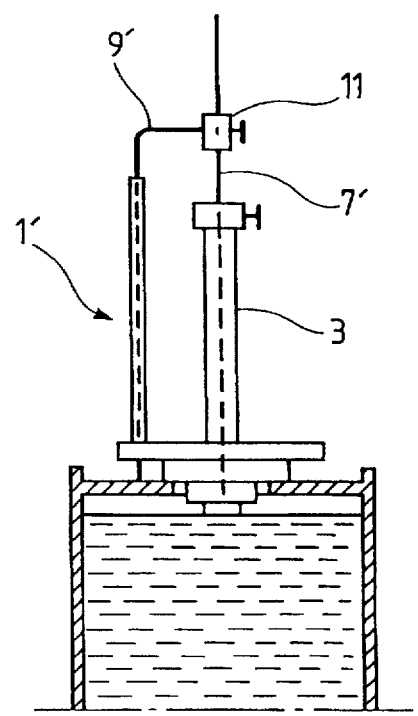
FIGS. 3A and 3B are diagrammatic views of an alternative embodiment of the device from FIG. 1.
Figure 3B:
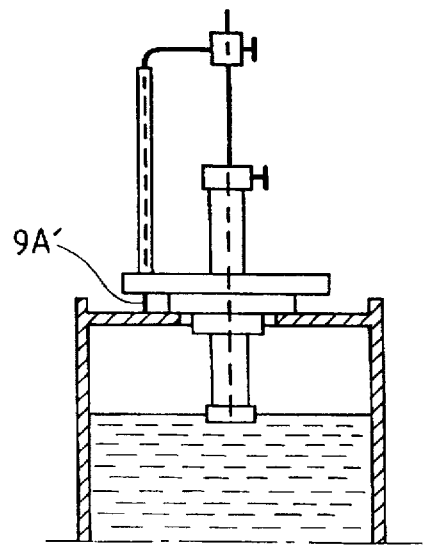
Figure 4:
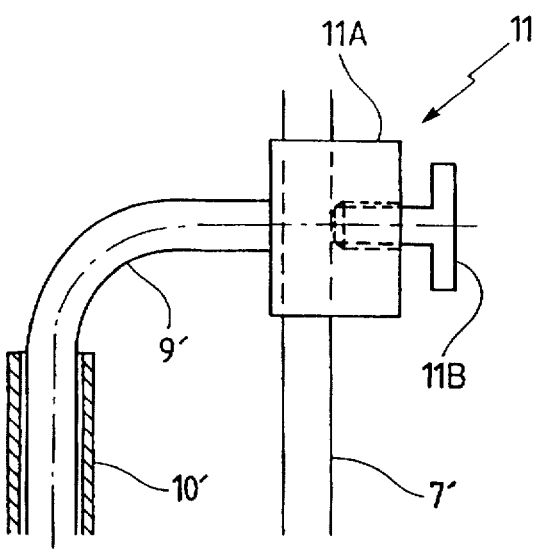
FIG. 4 is a detailed view showing the temporary coupling of the branches of the inverted U-shape from FIGS. 3A and 3B.

Alternatively, as shown in FIGS. 3A, 3B and 4, this generally U-shaped member can be in two separate parts: the rod 7' and an inverted J-shaped part 9' whose relative height can be varied by temporary fixing means 11 (components similar to those in FIG. 1 are identified by the same reference numbers "primed").

In this embodiment the temporary fixing means is a sleeve 11A attached to the branch 9' adapted to receive the piston rod 7' for sliding movement within it and provided with a clamping screw 11B.

The disk 8 and the abutted end of the bearing surface 9A' are at different levels and the difference can be modified by the fixing means 11 (FIG. 3A corresponds to a completely full drum while FIG. 3B corresponds to a partly full drum).

A device can be provided for locking the cup 2 in order to fix and/or seal it to the drum. For example it is possible to provide a screwthread on the outside of the lower part of the cup (for example the skirt 2B in FIG. 1) that can be used to screw the cup to all drums having a screwthreaded filler orifice.

A second piston disk 12 can be added below the piston disk 8, with a separate piston rod 13. The second piston disk 12 is then advantageously provided with a valve 20 enabling the fluid to flow only upwards after the body 3 is filled as previously described. The sample can be transferred directly into a sample flask merely by raising the second piston disk 12 by means of the piston rod 13 to expel the sample through a spout 30 formed in the wall of the body 3 near its upper end. The piston disks 8 and 12 must then be lowered again to discharge any products that may have been absorbed in the chamber during raising of the second piston disk 12.

The spout 30 is separated from the aspiration end-piece 4 by the disk 8 over only part of the relative sliding travel of the disk and the tube. In practice, it is beneficial if this spout is not uncovered by the disk 8 until the end of its upward travel.

Figure 5:
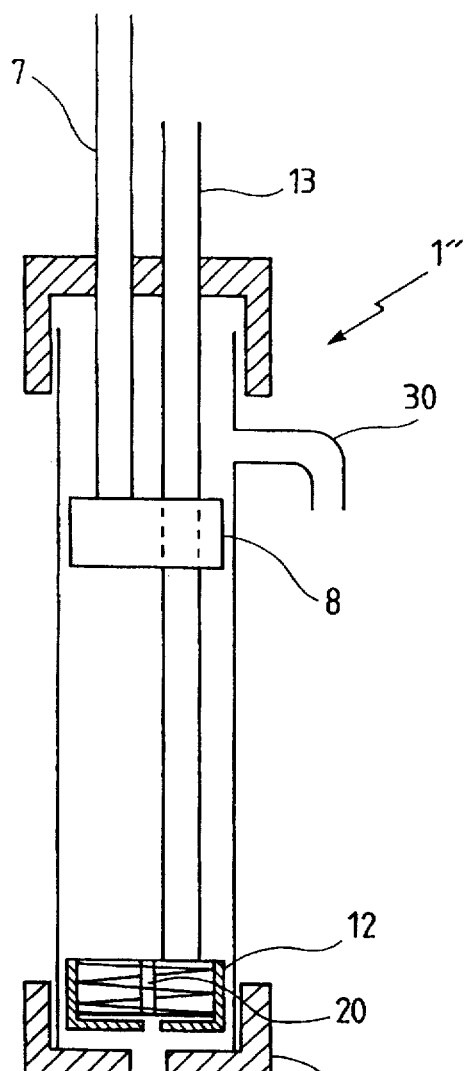
FIG. 5 is a diagrammatic view showing part of a further embodiment of the sampling device.

The device 1" shown in FIG. 5 is very practical when the operator has to work in a confined space. The sample is collected directly from the outlet of the spout 30 with the device still inserted into the drum. However, it is effective only if the products to be sampled are of the same kind and the drums are totally full, since it is difficult to clean the inside of the spout 30. Moreover, it is no longer possible to adjust the distance between the disk 8 and the bearing surface 9A on the other branch 9 (as described above) if the discharge spout or orifice 30 is to be kept outside the drum.

The second piston disk 12 can be substituted for the aspiration end-piece 4.

To facilitate relative adjustment of the bearing surface 9A and the disk 8 as described above, a level sensor (not shown, but of the contact type, for example), a float or any other indicator device, can be added to the sampling device (for example to the body 3) to tell the operator exactly when the end of the aspiration end-piece 4 with the disk comes into contact with the surface of the liquid contained in the container.

Figure 6:
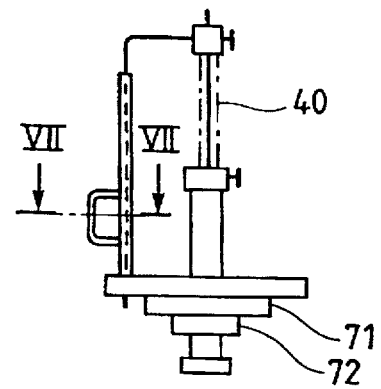
FIG. 6 is a diagrammatic view of another embodiment of the sampling device.

To make it easier to use, an adequately sized pneumatic actuator or any other device (diagrammatically shown at 40 in FIG. 6) can be added to the sampling device to move the body 3 over the travel needed to fill and to drain off the chamber 100.

Figure 8A:
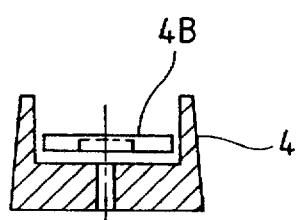
FIGS. 8A, 8B and 8C are top, side and vertical sectional views of an elastic lip seal
Figure 8D:
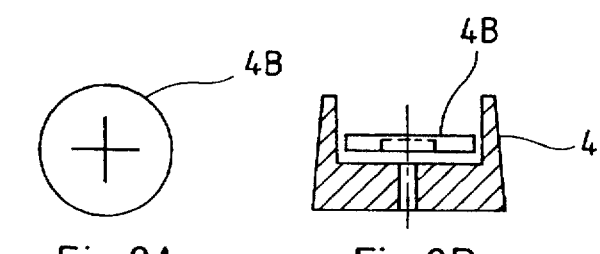
FIG. 8D is a view of this seal partly in section engaged in an end-piece of a dip-tube.
Figure 7:
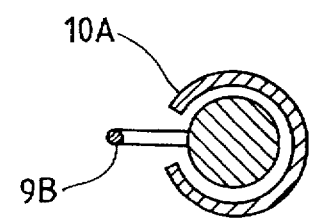
FIG. 7 is a view of part of the device from FIG. 6 in section taken on the line VII—VII.
Figures 8B, 8C:
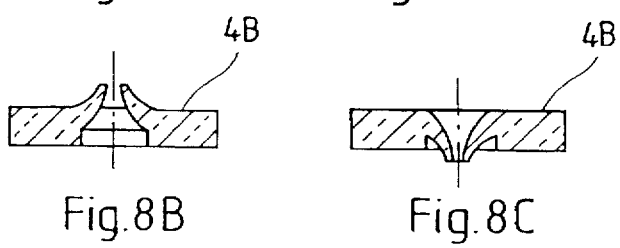

If the size of the aspiration hole 4A in the aspiration end-piece 4 is such that the liquids cannot be retained within the body 3, a lip-seal can be provided in the end-piece (see FIG. 8D) with the lips oriented towards the interior of the body (FIG. 8B) or towards its exterior (FIG. 8C), according to whether the fluid is to be aspirated or discharged. The seal allows the fluid to flow only when pressure is applied to the disk 8.

If the fluid must be discharged through the same hole, the moving part of the valve advantageously includes a projection (not shown) accessible from the outside to force it open, either manually or by abutment with a bearing surface on the sample flask into which the content of the chamber 100 is to be transferred.

To facilitate manipulation of the piston rod 7 by way of the branch 9 a longitudinal groove 10A can be provided on the sleeve 10 and a holding member such as a handle 9B fixed to the rod 9.

Plastic caps can be provided to protect the end surface of the end-piece 4; these caps can be disposable to eliminate the problem of cleaning the end of the end-piece 4.

The cup can include a plurality of annular centering steps 71 and 72 on the inside so that it can be used with more than one filler orifice diameter.

It goes without saying that the foregoing description has been given by way of non-limiting example only and that many variants can be suggested by the person skilled in the art without departing from the scope of the invention.

I claim:

1. A device for sampling fluid from a drum, said drum having a substantially horizontal wall with an orifice therein, said device comprising:

a columnar member having a bore therethrough, said columnar member having a lower end and an opposite upper end;

a closure member located at said lower end of said columnar member, said closure member having one way valve means for enabling said fluid to be aspirated into said columnar member and preventing said fluid from escaping from said columnar member as a result of the weight of said fluid;

a piston movably mounted within said columnar member between said opposite upper and said lower ends, said piston entering said columnar member through said opposite upper end, said piston having a rod portion and a disk portion mounted for slidable movement within said columnar member, said disk portion connected to an end of said rod portion, said disk portion having means for sealing located between said disk portion and said columnar member, said disk portion remaining fully inside said columnar member;

means for positioning said piston surrounding said columnar member, said means for positioning said piston comprising a support member resting on said substantially horizontal wall of said drum over said orifice, said support member having a passage in which said columnar member slides; and second means for sealing located between said columnar member and said support member, said second means for sealing further comprising means for scraping such that relative movement between said support member and said columnar member occurs as said means for scraping scraps the exterior surface of said columnar member.

2. A device according to claim 1 wherein said piston is a generally inverted U-shaped member, a first branch of said U-shaped member being constituted by said rod portion, a second branch of said U-shaped member having a bearing surface, said bearing surface adapted to bear on a reference surface for said support member, said branches of said U-shaped member being connected by said positioning means.

3. A device according to claim 2 wherein said reference surface is said substantially horizontal wall of said drum.

4. A device according to claim 3 wherein said second branch further comprises a guide sleeve attached to said support member at a distance from said passage.

5. A device according to claim 4 wherein said guide sleeve further comprises a longitudinal slot and said second branch further comprises holding means projecting radially from said guide sleeve through said longitudinal slot.

6. A device according to claim 2 wherein said reference surface is attached to said support member.

7. A device according to claim 2 wherein said first and second branches of said U-shaped member are fastened together.

8. A device according to claim 2 wherein said first and second branches of said U-shaped member further comprise means for adjusting their relative position.

9. A device according to claim 8 wherein said second branch further comprises a sleeve adapted to receive said rod portion, said second branch also having clamping means for immobilizing said columnar member.

10. A device according to claim 1 wherein said support member further comprises a plurality of annular centering steps for accommodating a plurality of orifice diameters.

11. A device according to claim 1 wherein said support member further comprises an externally threaded skirt.

12. A device according to claim 1 wherein said columnar member and said rod portion further comprise means for temporarily fixing said rod portion relative to said columnar member.

13. A device according to claim 1 wherein said closure member further comprises a hole for aspiration and discharge of said fluid.

14. A device according to claim 13 wherein said closure member hole has a diameter chosen according to a viscosity of said fluid for enabling aspiration and discharge of said fluid by relative movement of said piston while preventing said fluid from escaping said columnar member under its own weight.

15. A device according to claim 13 wherein said closure member hole further comprises a split elastic seal flanked by a lip.

16. A device according to claim 13 wherein said closure member hole is closed by an anti-leak valve, said anti-leak valve incorporating an opening member accessible from outside said device.

17. A device according to claim 1 wherein said columnar member further comprises a hole near said upper end for discharging said fluid, said discharge hole being located between said upper end and said lower end; and a second disk portion spaced from said disk portion, said second disk portion having a nonreturn valve for forcing discharge of said fluid by upward movement of said second disk portion.

18. A device according to claim 17 wherein said second disk portion constitutes said closure member.

19. A method of taking a sample of fluid from a drum filled to a given level within a mass of fluid, said method comprising the steps of:

immersing a columnar member having an entry orifice into said mass of fluid such that said entry orifice is in said mass of fluid;

sliding said columnar member about a disk portion which is sealed to said columnar member such that a constant distance is maintained between said disk portion and said mass of fluid whereby said sample of fluid is contained inside said columnar member, said sample of fluid enters said columnar member by aspiration through a closure member, said closure member having an orifice nonreturn means for preventing escape of said sample of fluid under its own weight;

removing said columnar member from said mass of fluid, said disk portion being held a fixed distance relative to said columnar member; and expelling said sample of fluid from said columnar member through a discharge hole, wherein said columnar member slides inside a scraper ring, said scraper ring being temporarily fixed to said disk portion.

20. A method according to claim 19 wherein during sampling said disk portion is positioned substantially level with a surface of said mass of fluid.

* * * * *